United States Patent
Fang et al.

(10) Patent No.: US 6,845,271 B2
(45) Date of Patent: Jan. 18, 2005

(54) TREATMENT OF SHOULDER DYSFUNCTION USING A PERCUTANEOUS INTRAMUSCULAR STIMULATION SYSTEM

(75) Inventors: Zi-Ping Fang, Mayfield Village, OH (US); Maria Walker, Shaker Heights, OH (US)

(73) Assignee: Neurocontrol Corporation, Valley View, OH (US)

( * ) Notice: Subject to any disclaimer, the term of this patent is extended or adjusted under 35 U.S.C. 154(b) by 0 days.

(21) Appl. No.: 10/138,791

(22) Filed: May 3, 2002

(65) Prior Publication Data

US 2003/0014088 A1 Jan. 16, 2003

Related U.S. Application Data

(63) Continuation-in-part of application No. 09/862,156, filed on May 21, 2001, which is a continuation of application No. 09/089,994, filed on Jun. 3, 1998, now abandoned.

(51) Int. Cl.[7] .................................................. A61N 1/36
(52) U.S. Cl. .......................................... 607/74; 607/50
(58) Field of Search ........................ 607/1, 2, 46, 48, 607/50, 63, 66, 68, 69–76

(56) References Cited

U.S. PATENT DOCUMENTS

| | | |
|---|---|---|
| 2,521,722 A | 9/1950 | Hubbell et al. |
| 3,067,401 A | 12/1962 | Rhodes |
| 3,568,675 A | 3/1971 | Harvey |
| 3,663,965 A | 5/1972 | Lee Jr., et al. |
| 3,701,080 A | 10/1972 | Baisz et al. |
| 3,850,161 A | 11/1974 | Liss |
| 3,964,470 A | 6/1976 | Trombley |
| 4,019,518 A | 4/1977 | Maurer et al. |
| 4,026,301 A | 5/1977 | Friedman et al. |
| 4,223,679 A | 9/1980 | Schulman et al. |

(List continued on next page.)

FOREIGN PATENT DOCUMENTS

| | | |
|---|---|---|
| EP | 0 165 049 A2 | 12/1985 |
| GB | 945482 | 1/1964 |
| GB | 2085733 | 5/1982 |
| GB | 2 123 698 A | 2/1984 |
| GB | 2 223 949 A | 5/1990 |
| RU | 1181671 | 9/1986 |

OTHER PUBLICATIONS

"Coordinated Two Mode Grasp in the Quadriplegic Initiated by Functional Neuromuscular Stimulation", P.H. Peckham et al.; IFAC Control Aspects of Prosthetics and Orthotics, Ohio USA, 1982.

NeuroControl Press Release Jan. 17, 2000 StIM ™System Receives CE mark approval.

(List continued on next page.)

*Primary Examiner*—George R. Evanisko (57) ABSTRACT

A method of treating shoulder dysfunction involves the use of a percutaneous, intramuscular stimulation system. A plurality of intramuscular stimulation electrodes are implanted directly into select shoulder muscles of a patient who has suffered a disruption of the central nervous system such as a stroke, traumatic brain injury, spinal cord injury or cerebral palsy. An external microprocessor based multi-channel stimulation pulse train generator is used for generating select electrical stimulation pulse train signals. A plurality of insulated electrode leads percutaneously, electrically interconnect the plurality of intramuscular stimulation electrodes to the external stimulation pulse train generator, respectively. Stimulation pulse train parameters for each of the stimulation pulse train output channels are selected independently of the other channels. The shoulder is evaluated for subluxation in more than one dimension. More than one muscle or muscle group is simultaneously subjected to a pulse train dosage. Preferably, the at least two dosages are delivered asynchronously to two muscle groups comprising the supraspinatus in combination with the middle deltoid, and the trapezious in combination with the posterior deltoid.

14 Claims, 8 Drawing Sheets

U.S. PATENT DOCUMENTS

| | | | |
|---|---|---|---|
| 4,250,882 A | 2/1981 | Adair |
| 4,281,664 A | 8/1981 | Duggan |
| 4,326,534 A | 4/1982 | Axelgaard et al. |
| 4,408,608 A | 10/1983 | Daly et al. |
| 4,413,314 A | 11/1983 | Slater et al. |
| 4,453,162 A | 6/1984 | Money et al. |
| 4,459,989 A | 7/1984 | Borkan |
| 4,528,984 A | 7/1985 | Morawetz et al. |
| 4,528,987 A | 7/1985 | Slocum |
| 4,532,932 A | 8/1985 | Batty, Jr. |
| 4,558,704 A | 12/1985 | Petrofsky |
| 4,561,443 A | 12/1985 | Hogrefe et al. |
| 4,569,352 A | 2/1986 | Petrofsky et al. |
| 4,579,120 A | 4/1986 | MacGregor |
| 4,586,510 A | 5/1986 | Glaser et al. |
| 4,595,010 A | 6/1986 | Radke |
| 4,622,973 A | 11/1986 | Agarwala |
| 4,632,116 A | 12/1986 | Rosen et al. |
| 4,639,667 A | 1/1987 | Andresen |
| 4,640,983 A | 2/1987 | Comte |
| 4,645,504 A | 2/1987 | Byers |
| 4,690,145 A | 9/1987 | King-Smith et al. |
| 4,693,254 A | 9/1987 | Mickiewicz et al. |
| 4,699,143 A | 10/1987 | Dufresne et al. |
| 4,793,353 A | 12/1988 | Borkan |
| 4,942,514 A | 7/1990 | Miyagaki et al. |
| 4,990,258 A | 2/1991 | Bjare et al. |
| 5,063,929 A | 11/1991 | Bartelt et al. |
| 5,092,329 A | 3/1992 | Graupe et al. |
| 5,167,229 A | 12/1992 | Peckham et al. |
| 5,247,434 A | 9/1993 | Peterson et al. |
| 5,285,781 A | 2/1994 | Brodard |
| 5,300,096 A | 4/1994 | Hall et al. |
| 5,581,687 A | 12/1996 | Lyle et al. |
| 5,609,770 A | 3/1997 | Zimmerman et al. |
| 5,653,887 A | 8/1997 | Wahl et al. |
| 5,702,428 A | 12/1997 | Tippey et al. |
| 5,800,458 A | 9/1998 | Wingrove |
| 5,836,995 A | 11/1998 | MGraw et al. |
| 5,861,017 A | 1/1999 | Smith et al. |
| 5,983,140 A | 11/1999 | Smith et al. |
| RE36,690 E | 5/2000 | McGraw et al. |
| 6,163,725 A | 12/2000 | Peckham et al. |
| 6,315,721 B2 | 11/2001 | Schulman et al. |
| 6,456,884 B1 * | 9/2002 | Kenney ........................ 607/48 |

OTHER PUBLICATIONS

NeuroControl StIM™ System Brochure; circa Jan. 2000.

The NeuroControl StIM ™ System Brochure; circa Jan. 2000.

"Electronic Detours of Broken Nerve Paths", by L. Vodovnik et al., Electronics, Sep. 20, 1965, pp. 110–116.

"Remote Monitoring . . . in Unrestrained Cats", by Prochazka et al., Electroencephalography ∉ Clin. Neurophysiology, vol. 37. No. 6, Dec. 1974, pp. 649–653.

"Mobility Aid for Quadriplegics ", Maass et al., 1973, Carnahan Conference on Electronic Prosthesis, Lexington, KY; Sep. 19–21, 1973; pp. 123–125.

"Design and Fabrication for Experimental Cochlear Prosthesis", Leob et al., Med ∉ Biomed Eng. ∉ Comput. May 1983, pp. 241–253.

"Restoration of Hand Function in the Quadriplegic Through Electrical Stimulation", Peckham et al., Functional Electrical Stimulation, Hanbrecht ∉ Reswick, 1977, pp. 83–95.

"A Portable Microprocessor Controlled Implantable Functional Neuromuscular Stimulation System", Smith et al., Proceedings fo the $2^{nd}$ Int. Conf. On Rehab., Eng. 1984.

"A Microprocessor Based Portable Functional Electrical Stimulation System", Buckett et al., $6^{th}$ Annual Conference on Rehabilitation Eng., San Diego, CA 1983, pp. 72–74.

"Theoretical Design and Implementation of a Transcutaneous, Multichannel Stimulator for Neural Prosthesis Applications", Forster; J. Biomed. Eng. vol. 3, No. 2, Apr. 1981; pp. 107–120.

"Shoulder Position Control, An Alternative Control Technique for Motion Impaired Individuals ", Buckett et al., Proceed of Int'l Conference on Rehabilitation Engineering, Toronto 1980, pp. 224–247.

"Multichannel Implantable Stimulator for Control of Paralyzed Muscle", Peckham et al., IEE Trans on Biomed. Eng., V. BME.

"Proportional Joystick Controller for High Level Quadriplegics", Thrope et al., RESNA $8^{th}$ Annual Conference; Memphis, TN 1985 pp. 401–403.

"Design and Control of a Manipulator for Tertraplegics" by Paeslack et al., Mechanism & Machine Theory 1977, vol. 12, No. 5, pp. 413–423.

"EMG Controlled Functional . . . of the Paretic Hand", G. Hansen; Scan J. Rehab Med 11, 1979, pp. 189–193.

"Programmed Six Channel. . . During Walking", P. Strojnkik et al., IEEE Trans. On Biomend, Eng., vol. BME: 26, No. 2, Feb. 79; pp. 112–116.

"Proportionally Controlled Functional Electrical Stimulation of the Hand", S. Rebersek et al., Arch Phys Med Rehabilitation, vol. 54, Aug. 1973, pp. 378–382.

"A Computer Controlled Multichannel Stimulation System for Laboratory Use in Functional Neuromuscular Stimulation", Thrope et al., IEEE Transactions on Biomedical Engineering, vol. BME–32, No. 6, Jun. 111985; pp. 363–370.

"Controlled Prehension and Release in the C5 Quadriplegic Elicited by Functional Electrical Stimulation of the Paralyzed Forearm Musculature", Peckham et al., Annals of Biomedical Engineering, vol. 8, pp. 368–388, 1980.

"Restoration of Key Grip and Release in the C5 and C6 Tetraplegic Through Functional Electrical Stimulation", Peckham et al., Proceeding fo International Conference on Rehabilitation Engineering Toronto, Canada 1980, pp. 227–229.

"Alteration in the Force and Fatigability of Skeletal Muscle in Quadriplegic Humans Following Exercise Induced by Chronic Electrical Stimulation", Peckham et al., Clinical Orthopaedics and Related Research; No. 114, Jan–Feb. 1976, pp. 326–344.

"Closed Loop Control of Force During Electrical Stimulation of Muscle", Crago et al., IEEE Transactions on Biomedical Engineering, vol. MBE–27, No. 6, Jun. 1980, pp. 306–312.

"An Implantable RF–Powered Dual Channel Stimulator", Poon et al., Biotelemetry Patient Monitoring, vol. 8, No. 3, pp. 180–188 (1981).

* cited by examiner

TREATMENT OF SHOULDER DYSFUNCTION USING A PERCUTANEOUS INTRAMUSCULAR STIMULATION SYSTEM

RELATED APPLICATIONS

This application is a continuation-in-part of copending patent application Ser. No. 09/862,156 filed May 21, 2001, which is a continuation of application Ser. No. 09/089,994 filed Jun 3, 1998, now abandoned and is related to provisional application Ser. No. 60/174,886 filed Jan. 7, 2000 and is further related to application Ser. No. 09/755,871 filed Jan. 6, 2001, now abandoned all of which are incorporated herein by reference.

FIELD OF THE INVENTION

The present invention relates to the art of therapeutic neuromuscular stimulation. It finds particular application for use by human patients who are paralyzed or partially paralyzed due to cerebrovascular accidents such as stroke or the like. The invention is useful for retarding, preventing muscle disuse atrophy and even improving muscular condition, maintaining or improving extremity range-of-motion, facilitating voluntary motor function, relaxing spastic muscles, and increasing blood flow to select muscles of the shoulder. Additional benefits of the invention may include improved alignment and decreased pain.

BACKGROUND OF THE INVENTION

The invention is particularly useful for the treatment of shoulder dysfunction. An estimated 555,000 persons are disabled each year in the United States of America by cerebrovascular accidents (CVA) such as stroke. Many of these patients are left with partial or complete paralysis of an extremity including for example, hemiplegic subluxation (incomplete dislocation) of the shoulder joint. This is a common occurrence and has been associated with chronic and debilitating pain among stroke survivors. In stroke survivors experiencing shoulder pain, motor recovery is frequently poor and rehabilitation is impaired. Thus, the patient may not achieve his/her maximum functional potential and independence. Therefore, prevention and treatment of subluxation in stroke patients is a priority.

There is a general acknowledgment by healthcare professionals of the need for improvement in the prevention and treatment of shoulder subluxation. Conventional intervention includes the use of orthotic devices; such as slings and supports, to immobilize the joint in an attempt to maintain normal anatomic alignment. The effectiveness of these orthotic devices varies with the individual. Also, many authorities consider the use of slings and arm supports to be controversial or even contraindicated because of the potential complications from immobilization including disuse atrophy and further disabling contractures.

Surface, (i.e., transcutaneous) electrical muscular stimulation has been used therapeutically for the treatment of shoulder subluxation and associated pain, as well as for other therapeutic uses. Therapeutic transcutaneous stimulation has not been widely accepted in general because of stimulation-induced pain and discomfort, poor muscles selectivity, and difficulty in daily management of electrodes, which necessitates a highly specialized clinician for treatment. In addition to these electrode-related problems, commercially available stimulators are relatively bulky, have high-energy consumption, and use cumbersome connecting wires.

In light of the foregoing deficiencies, transcutaneous stimulation systems are typically limited to two stimulation output channels. The electrodes mounted on the surface of the patient's skin are not able to select muscles to be stimulated with sufficient particularity and are not suitable for stimulation of the deeper muscle tissue of the patient as required for effective therapy. Any attempt to use greater than two surface electrodes on a particular region of a patient's body is likely to result in suboptimal stimulation due to poor muscle selection. Further, transcutaneous muscle stimulation via surface electrodes commonly induces pain and discomfort.

Studies suggest that conventional interventions are not effective in preventing or reducing long term pain or disability. Therefore, it has been deemed desirable to develop a therapy for the treatment of shoulder dysfunction which involves the use of a percutaneous, (i.e., through the skin,) neuromuscular stimulation system having implanted, intramuscular stimulation electrodes connected by percutaneous electrodes leads to an external and portable pulse generator.

SUMMARY OF THE INVENTION

In accordance with the first aspect of the present invention, a therapy involves therapeutic electrical stimulation of select shoulder muscles of a patient. The therapy includes the implantation of a plurality of intramuscular stimulation electrodes directly into selected shoulder muscles of a patient near the muscle motor point. This avoids stimulation of cutaneous nociceptors; requires lower stimulus intensities and avoids uncomfortable stimulation of adjacent non-target muscles. The electrodes are addressed using an external battery-operated, microprocessor-based stimulation pulse train generator, which generates select electrical stimulation pulse train signals. Preferably, the pulse train generator is portable and in particular is miniaturized to a convenient size. This pulse train generator includes a plurality of electrical stimulation pulse train output channels connected respectively to the plurality of percutaneous electrode leads. Stimulation pulse train parameters are selected for each of the stimulation pulse train output channels independently of the other channels. Muscle selection was determined generally by three-dimensional radiographic evaluation of a number of patients along with selective stimulation of all of the shoulder muscles. Ultimately it was determined that a preferred therapy involved asynchronous stimulation of more than one muscle group and more preferably with a first muscle group being the supraspinstus in combination with the middle deltoid and a second muscle group being the trapezious in combination with the posterior deltoid. The stimulation pulse train parameters or regiment or dosage include at least pulse amplitude and pulse width or duration for stimulation pulses of the stimulation pulse train, and an interpulse interval between successive pulses of the stimulation pulse train defining a pulse frequency.

Advantageously, the therapy involves the asynchronous stimulation of more than one muscle or muscle group. This asynchronous stimulation involves intermittent periods of stimulation and rest with different pulse train envelop delivered to the multiple sites but not in a synchronized dose. Thus, one muscle or muscle group may be resting while another muscle or muscle group may be subjected to stimulation. In the simplest case, these two dosages are the same but offset in time. With the therapy of the present invention more than one stimulation cycle is delivered at a point in time so that a first cycle may be delivered to a first muscle or muscle group with a second muscle or group undergoing a second stimulation cycle (which can be a straight, low-level stimulation or a cycle having a different profile, or can be the same cycle applied at a different point in time). In general, the electrical stimulators include means for generating stimulation pulse train signals with the selected pulse train parameters on each of the plurality of stimulation pulse train output channels so that stimulus pulses of the pulse train signals having the select stimulation pulse train parameters pass between the intramuscular electrodes respectively connected to the stimulation pulse train output channels and a reference electrode.

In accordance with another aspect of the invention, a method of stimulating select shoulder muscle tissue of a patient includes programming a patient external stimulation pulse generator with at least one stimulation pulse train session including at least one stimulation cycle (and preferably at least two stimulation cycles) defining a stimulation pulse train envelope for a plurality of stimulation pulse train output channels. Each envelope is defined by at least a ramp-up phase of a first select duration wherein pulses of a stimulus pulse train progressively increase in charge, a hold phase of a second select duration wherein pulses of the stimulus pulse train are substantially constant charge, and a ramp-down phase of a third select duration wherein pulses of the stimulus pulse train progressively decrease in charge. During a second hold phase there is no stimulus delivered and the muscles are allowed to relax or rest. In accordance with the invention, two muscle groups are subjected to a first and a second stimulation cycles so that one set of muscles is stimulated during the rest cycle of the second set of muscles. This inhibits the shoulder from slipping back into misalignment during the rest portion of the cycle. A plurality of intramuscular electrodes are implanted into select shoulder muscle tissue of the patient and electrically connected by percutaneous electrode leads to the plurality of output channels, respectively, of the pulse train generator. On each of said plurality of stimulation output channels and in accordance with a respective envelope, stimulation pulse train signals are generated with the generator so that the select muscle tissue of the patient is stimulated in accordance with the at least one stimulation cycle.

Further in accordance, one advantage of the present invention is the provision of a therapeutic percutaneous intramuscular stimulation system that retards or prevents muscle disuse atrophy, maintains muscle range-of-motion, facilitates voluntary motor function, relaxes spastic muscles, and increases blood flow in selected muscles.

Another advantage of the present invention is that it provides a therapeutic muscular stimulation system that uses intramuscular, rather than skin surface (transcutaneous) electrodes to effect muscle stimulation of select shoulder muscles.

Yet another advantage of the present invention is that the treatment dosage or regiment, which is prescribed may be tailored to suit individual needs and selectively varied even during the course of treatment. For example, the stimulus may be titrated at the onset to avoid pain and unwanted joint movement (such as for example, active elbow flexion during biceps stimulation).

In a further embodiment of the invention, a method of therapy is provided for treatment of shoulder dysfunction (such as subluxation) which comprises the steps of: 1) radiographic evaluation of the shoulder in at least two planes (preferably the subluxation is evaluated in 3-dimentisons); 2) percutaneous implantation of two or more electrodes, so as to contact a muscle or nerve, the electrode being in electrical communication with a pulse train generator; and 3) actuation of the pulse train generator in accordance with a regiment or prescribed dosage to cause stimulation of the muscle or nerve using the electrodes. The regiment or course of treatment may be a pre-defined course of treatment based on a stimulation pattern, which has been stored in a host computer or integral microprocessor, which can be used to address the pulse train generator. Preferably, the regiment will include individual sessions having a ramped profile and including intermittent stimulation activation of the electrode or electrodes with periods of rest. Preferably, the treatment of shoulder subluxation involves implantation of one or more electrodes into the superspinatus as well as into the posterior, middle and anterior deltoids; into the coracolbrachialis; into the biceps and triceps longhead. Even more preferably the treatment accounts for shoulder relocation in three dimensions with a focus on stimulation of all heads of the deltoid, the coracobrachialis, the biceps and the triceps longhead. Modulation of the stimulus may require precise muscle activation to balance against agonist and antagonist activity to avoid undesirable joint translation and rotation.

BRIEF DESCRIPTION OF THE DRAWINGS

The invention may take form in various components and arrangements of steps. The drawings are only for purposes of illustrating preferred embodiments, and are not to be construed as limiting the invention.

DETAILED DESCRIPTION OF THE INVENTION

With reference to FIGS. 1A–1D, a percutaneous, intramuscular stimulation system is shown which can be used with the method of treating shoulders in accordance with the present invention. The stimulator includes an electrical stimulation pulse generator 10. The pulse generator 10 includes a lightweight, durable plastic housing 12 fabricated from a suitable plastic or the like. The case 12 includes a clip 14 that allows the pulse generator 10 to be releasably connected to a patient's belt, other clothing, or any other convenient location. The case 12 also includes a releasable battery access cover 16.

For output of visual data to a patient or clinician operating the stimulation system, a visual display 20 is provided. The display 20 is preferably provided by a liquid crystal display, but any other suitable display means may alternatively be used. An audio output device, such as a beeper 22 is also provided.

For user control, adjustment, and selection of operational parameters, the stimulation pulse generator 10 includes means for input of data. Preferably, the pulse generator 10 includes an increment switch 24, a decrement switch 26, and a select or "enter" switch 28. The increment and decrement switches 24, 26 are used to cycle through operational modes or patterns and stimulation parameters displayed on the display 20, while the select switch 28 is used to select a particular displayed operational pattern or stimulation parameter. The select switch 28 also acts as a power on/off toggle switch.

For output of electrical stimulation pulse train signals, the pulse train generator 10 includes an external connection socket 30 that mates with a connector of an electrode cable assembly (not shown) to interconnect the pulse generator 10 with a plurality of intramuscular electrodes via percutaneous electrode leads. More particularly, the cable assembly connected to the socket 30 includes a second connector on a distal end that mates with a connector attached to the proximal end of each of the percutaneous stimulation electrode leads and a reference electrode lead.

Figure 1A:
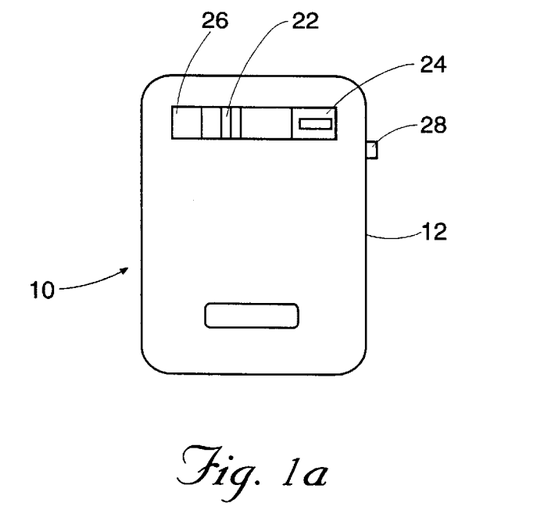
FIG. 1A is a front elevational view of a portable, programmable stimulation pulse train generator in accordance with the present invention.
Figure 1B:
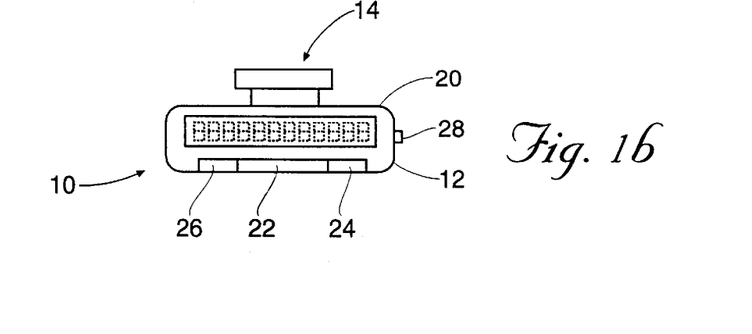
FIGS. 1B–1D are top, bottom, and right-side elevational views of the stimulation pulse train generator of FIG. 1A.
Figure 1C:
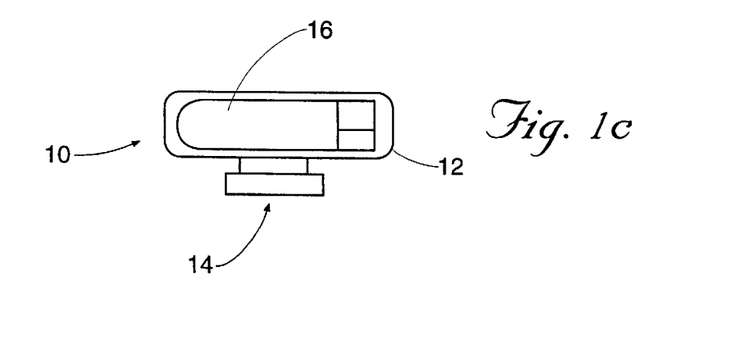
Figure 1D:
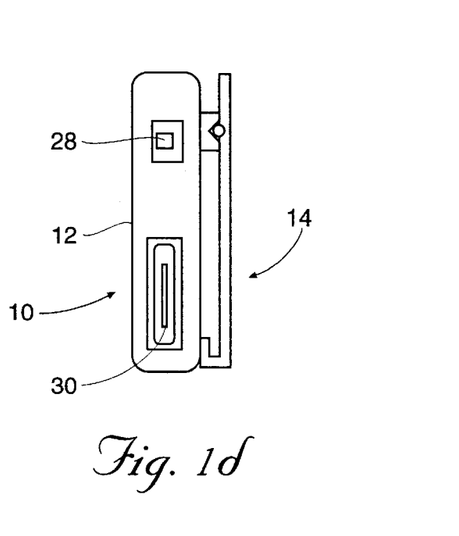
Figure 2:
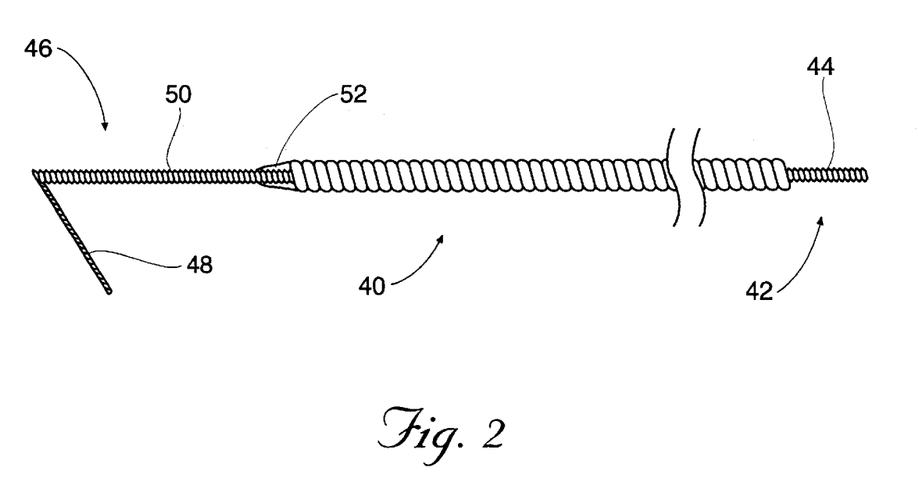
FIG. 2 illustrates a preferred intramuscular electrode and percutaneous electrode lead.

A suitable intramuscular electrode and percutaneous lead are shown in FIG. 2. The electrode lead 40 is fabricated from a 7-strand stainless steel wire insulated with a biocompatible polymer. Each individual wire strand has a diameter of 34 $\mu$m and the insulated multi-strand lead wire has a diameter of 250 $\mu$m. The insulated wire is formed into a spiral or helix as has been found preferred to accommodate high dynamic stress upon muscle flexion and extension, while simultaneously retaining low susceptibility to fatigue. The outer diameter of the helically formed electrode lead 40 is approximately 580 $\mu$m and it may be encased or filled with silicone or the like.

As mentioned above, a proximal end 44 of each of the plurality of intramuscular electrode lead wires 40 are located exterior to the patient's body when in use. The proximal end 44 includes a deinsulated length for connection to an electrical connector in combination with the remainder of the electrode leads. The distal end 46 of each lead 40, which is inserted directly into muscle tissue, also includes a deinsulated length, which acts as the stimulation electrode 50. It is preferred that at least a portion of the deinsulated length be bent or otherwise deformed into a barb 48 to anchor the electrode in the selected muscle tissue. A taper 52, made from silicone adhesive or the like, is formed between the deinsulated distal end 50 and the insulated portion of the lead 40 to reduce stress concentration.

Unlike surface electrodes which are applied to the surface of the patient's skin using an adhesive, each of the plurality of percutaneous electrodes 50 is surgically implanted or inserted into select patient shoulder, arm, or upper-trunk muscle tissue, and the associated electrode lead 40 exits the patient percutaneously, i.e., through the skin, for connection to the stimulation pulse generator 10. Preferably, each of the electrodes 50 is implanted or inserted into the select muscles by use of a hypodermic needle. Alternatively, or in addition, muscles may be surgically exposed for implantation or minimally invasive techniques such as arthroscopy may be used. Once all of the electrodes are implanted as desired, their proximal ends are crimped into a common connector that mates with the cable assembly which is, in turn, connected to the pulse generator 10 through the connection socket 30. Of course, such therapies or uses may require multiple systems, which utilize multiple pulse train generators with multiple common connectors.

The present percutaneous, intramuscular stimulation system allows for precise muscle selection and use of three or more stimulation electrodes and channels. The preferred system in accordance with the present invention uses up to eight or more intramuscular electrodes 50, each connected to an independent electrode stimulation channel E, and a single reference electrode 52 which may be either an intramuscular or surface electrode.

The stimulation pulse generator 10 comprises a microprocessor-based stimulation pulse generator circuit with a micro controller such as a Motorola 68HC12. Operational instructions or other information are stored in non-volatile storage. Set stimulation therapy or patterns may be included in this storage. These therapies may be based upon generalized information such as may be gathered from radiographic evaluation in multiple dimensions along with selected stimulation. Ultimately patient specific information may be incorporated into the stimulation parameters in order to optimize the therapy for a particular individual application. Preferably, the nonvolatile memory also provides storage for all patient-specific stimulation protocols. A real time clock is provided as part of the circuit.

The electrical stimulator current passes between the selected electrodes and the reference electrode. A pulse duration timer provides timing input PDC as determined by the CPU to the pulse amplitude/duration controller to control the duration of each stimulation pulse. Likewise, the CPU provides a pulse amplitude control signal to the circuit by way of the serial peripheral interface to control the amplitude of each stimulation pulse. One suitable circuit means for output of stimulation pulses as described above is in accordance with that described in U.S. Pat. No. 5,167,229, the disclosure of which is hereby expressly incorporated by reference. An impedance detection circuit is used to monitor the therapy.

Each output channel E1–E8 includes independent electrical charge storage means such as a capacitor SC which, is charged to the high voltage $V_H$ through a respective current limiting diode CD. To generate a stimulation pulse, the microcontroller output circuit 102 provides channel select input data to switch component, as to the particular channel E1–E8 on which the pulse is to be passed. Switch means SW closes the selected switch $SW_1$–$SW_8$ accordingly. The microcontroller also provides a pulse amplitude control signal PAC into a voltage-controlled current source VCCS. As such, the pulse amplitude control signal PAC controls the magnitude of the current I, and the circuit VCCS ensures that the current I is constant at that select level as dictated by the pulse amplitude control input PAC. For stimulation of human muscle, it is preferably that the current I be within an approximate range of 1 mA–20 mA.

Upon completion of the cathodic phase $Q_C$ as controlled by the pulse duration control signal PDC, the discharged capacitor SC recharges upon opening of the formerly closed one of the switches $SW_1$–$SW_8$. The flow of recharging current to the capacitor SC results in a reverse current flow between the relevant electrode 50 and the reference electrode 52, thus defining an anodic pulse phase $Q_a$. The current amplitude in the anodic pulse phase $Q_a$ is limited, preferably to 0.5 mA, by the current limiting diodes CD. Of course, the duration of the anodic phase is determined by the charging time of the capacitor SC, and current flow is blocked upon the capacitor becoming fully charged. It should be recognized that the interval between successive pulses or pulse frequency PF is controlled by the CPU 62 directly through output of the channel select, pulse amplitude, and pulse duration control signals as described at a desired frequency PF.

A preferred design implements from 2 to 8 or more independent preprogrammed patterns. For each pattern, a stimulation session S is pre-programmed into the stimulator circuit by a clinician through use of the input means. Each session S has a maximum session duration of approximately 9 hours, and a session starting delay D. The maximum session starting delay D is approximately 1 hour. The session starting delay D allows a patient to select automatic stimulation session start at some future time. Within each session S, a plurality of stimulation cycles C are programmed for stimulation of selected muscles. Preferably, each stimulation cycle ranges from 2–100 seconds in duration.

Figure 3:
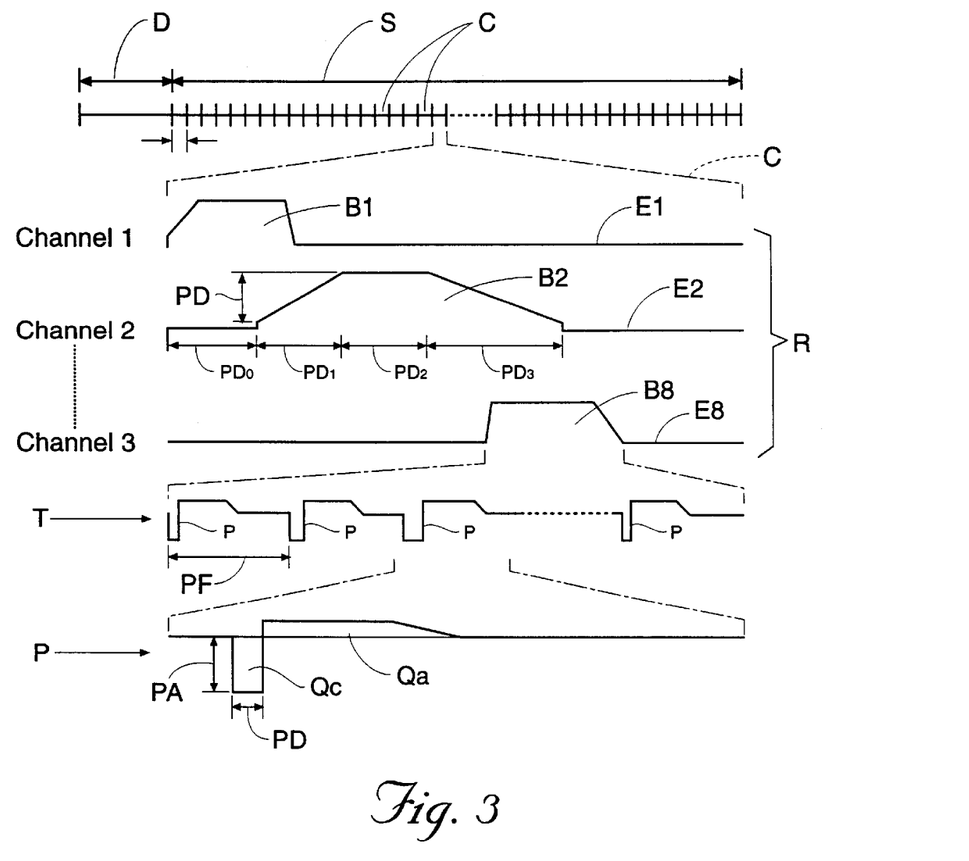
FIG. 3 graphically illustrates the stimulation paradigm of the percutaneous intramuscular stimulation system in accordance with the present invention.

With continuing reference to FIG. 3, a stimulus pulse train T includes a plurality of successive stimulus pulses P. As is described above and in the aforementioned U.S. Pat. No. 5,167,229, each stimulus pulse P is current-regulated and diphasic, i.e., comprises a cathodic charge phase $Q_c$ and an anodic charge-phase $Q_a$. The magnitude of the cathodic charge phase $Q_c$ is equal to the magnitude of the anodic charge phase $Q_a$. The current-regulated, biphasic pulses P provide for consistent muscle recruitment along with minimal tissue damage and electrode corrosion.

Each pulse P is defined by an adjustable pulse amplitude PA and an adjustable pulse duration PD. The pulse frequency PF is also adjustable. Further, the pulse amplitude PA, pulse duration PD, and pulse frequency PF are independently adjustable for each stimulation channel E. The amplitude of the anodic charge phase $Q_a$ is preferably fixed at 0.5 mA, but may be adjusted if desired.

Pulse "ramping" is used at the beginning and end of each stimulation pulse train T to generate smooth muscle contraction. Ramping is defined herein as the gradual change in cathodic pulse charge magnitude by varying at least one of the pulse amplitude PA and pulse duration PD. In FIG. 3, the preferred ramping configuration is illustrated in greater detail. As mentioned, each of the plurality of stimulation leads/electrodes 40,50 is connected to the pulse generator circuit 60 via a stimulation pulse channel E. As illustrated in FIG. 3, eight stimulation pulse channels E1,E2,E8 are provided to independently drive up to eight intramuscular electrodes 50. Stimulation pulse trains transmitted on each channel E1–E8 are transmitted within or in accordance with a stimulation pulse train envelope B1–B8, respectively. The characteristics of each envelope B1–B8 are independently adjustable by a clinician for each channel E1–E8. Referring particularly to the envelope B2 for the channel E2, each envelope B1–B8 is defined by a delay or "off" phase $PD_0$ where no pulses are delivered to the electrode connected to the subject channel, i.e., the pulses have a pulse duration PD of 0. Thereafter, according to the parameters programmed into the circuit 60 by a clinician, the pulse duration PD of each pulse P is increased or "ramped-up" over time during a "ramp-up" phase $PD_1$ from a minimum value (e.g., 5 $\mu$sec) to a programmed maximum value. In a pulse duration "hold" phase $PD_2$, the pulse duration PD remains constant at the maximum programmed value. Finally, during a pulse duration "ramp-down" phase $PD_3$, the pulse duration PD of each pulse P is decreased over time to lessen the charge delivered to the electrode 50.

This "ramping-up" and "ramping-down" is illustrated even further with reference to the stimulation pulse train T which is provided in correspondence with the envelope B8 of the channel E8. In accordance with the envelope B8, the pulse P of the pulse train T first gradually increase in pulse duration PD, then maintain the maximum pulse duration PD for a select duration, and finally gradually decrease in pulse duration PD.

As mentioned, the pulse amplitude PA, pulse duration PD, pulse frequency PF, and envelope B1–B8 are user-adjustable for every stimulation channel E, independently of the other channels. Preferably, the stimulation pulse generator circuit 60 is pre-programmed with up to four stimulation patterns, which will allow a patient to select the prescribed one of the patterns as required during therapy.

Most preferably, the pulse generator 10 includes at least up to eight stimulation pulse channels E. The stimulation pulse trains T of each channel E are sequentially or substantially simultaneously transmitted to their respective electrodes 50. The pulse frequency PF is preferably adjustable within the range of approximately 5 Hz to approximately 50 Hz; the cathodic amplitude PA is preferably adjustable within the range of approximately 1 mA to approximately 20 mA; and, the pulse duration PD is preferably adjustable in the range of approximately 5 $\mu$sec to approximately 200 $\mu$sec, for a maximum of approximately 250 pulses per second delivered by the circuit 60.

Figure 4:
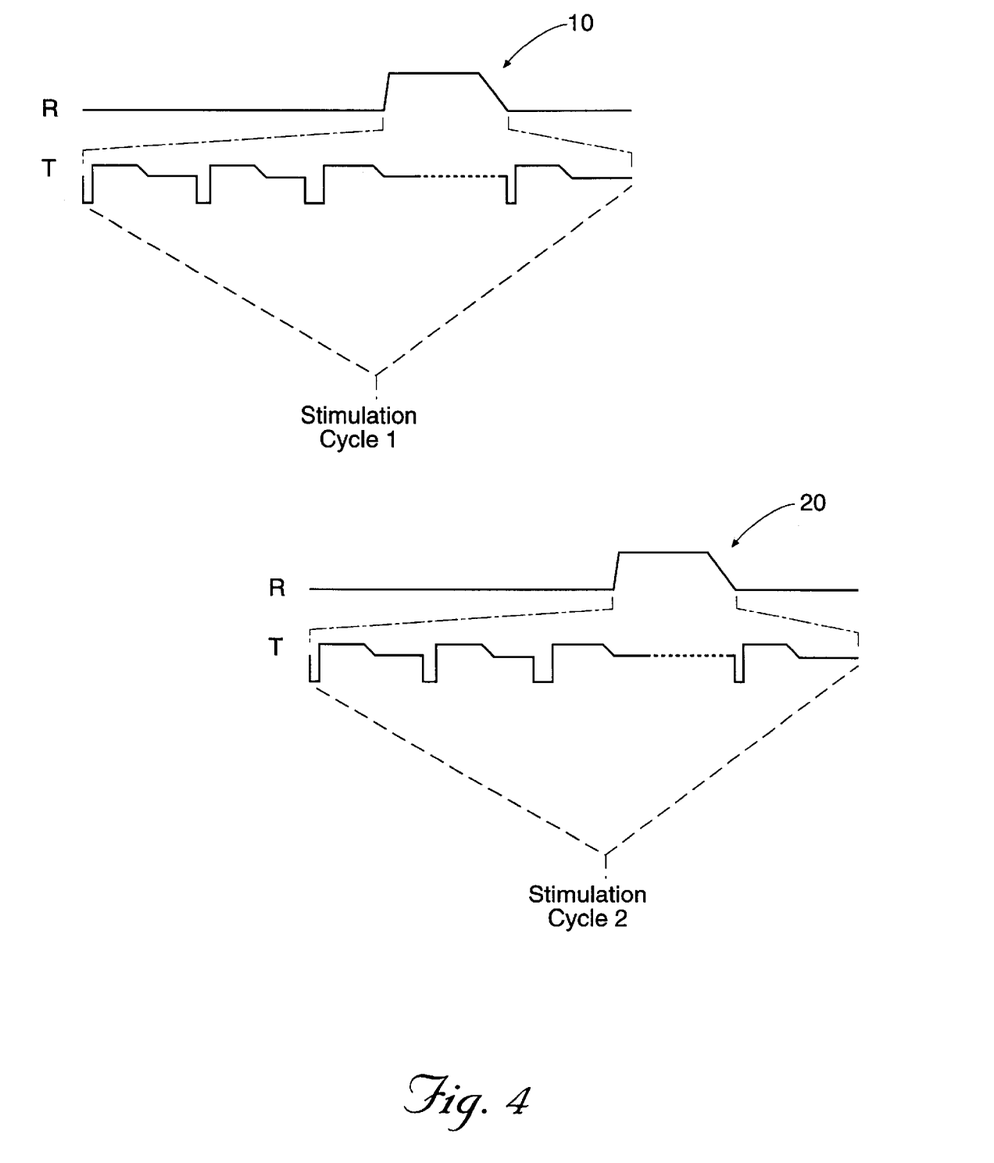
FIG. 4 graphically illustrates the preferred stimulation paradigm.

FIG. 4 illustrates an asynchronous stimulation profile consisting of a first stimulation cycle 10 administered to a first muscle group, i.e. the posterior deltoid and the supraspinatus, and a second stimulation cycle 20 which has the same stimulation profile but is offset from the first cycle and is administered to a second muscle group, i.e. the middle deltoid in combination with the upper trapezious. This method of treatment inhibits the misalignment, which might otherwise occur during the rest portion of the cycle.

In a further embodiment of the invention, a method of therapy is provided for treatment of shoulder dysfunction (such as subluxation) which comprises the steps of: 1) percutaneous implantation of two or more electrodes, so as to contact a muscle or nerve, the electrode being in electrical communication with a pulse train generator; and 2) actuation of the pulse train generator in accordance with a regiment or prescribed dosage to cause stimulation of the muscle or nerve using the electrodes which dosage has been defined as a result of a radiographic evaluation in three-dimensions (i.e. from multiple views including anterior-posterior, lateral) of a shoulder. The regiment or course of treatment may be a pre-defined course of treatment based on a stimulation pattern, which has been stored in a host computer or integral microprocessor, which can be used to address the pulse train generator. Preferably, the regiment will include individual sessions having a ramped profile and including intermittent stimulation activation of the electrode or electrodes with periods of rest. Preferably, the treatment of shoulder subluxation involves implantation of one or more electrodes into the superspinatus as well as into the posterior, middle and anterior deltoids; into the coracolbrachialis; into the biceps and triceps longhead. Even more preferably the treatment accounts for shoulder relocation in three dimensions with a focus on stimulation of all heads of the deltoid, the coracobrachialis, the biceps and the triceps longhead.

Modulation of the stimulus may require precise muscle activation to balance against agonist and antagonist activity to avoid undesirable joint translation and rotation.

The preferred treatment regiment is illustrated in FIG. 4 and thus therapy involves two stimulation cycles applied asynchronously. Each cycle has a 30±10 seconds period with 3–8; preferably 5±1 seconds each of ramp on and off and 5–15, preferably 10±2 seconds of hold. One cycle is applied to the posterior deltoid in combination with the supraspinatus while the other cycle is applied at a 5±5 second offset to the middle deltoid in combination with the upper trapezoidious. The cycle utilizes a balanced charge wave-form meaning that each pulse has an equal amount of positive and negative charge in each pulse. The envelope illustrates the outline of the amplitude of multiple pulses. The treatment generally involves weekly to daily periods of treatment for several minutes up to several hours. One postulated treatment involves 5–480 minutes of treatment, 1–3 times daily for 4–16 weeks. A preferred dosage us 4–7, preferably 6 hours per day for 6 weeks. Various muscles can undergo passive stimulation during the course of the day. The pulse train generator is miniature so that it is easily portable. Further, it provides multiple channels to allow a therapy or treatment use involving multiple nerves and/or multiple muscles. It is envisioned that the method of the present invention may have use in the treatment of acute and/or chronic dysfunction including the treatment of pain. For the treatment of shoulder dysfunction in hemiplegics (i.e., one sided paralysis) the therapy may even begin immediately upon presentation of stroke symptoms as a prophalalic treatment with respect to shoulder subluxation. The treatment is envisioned for indications involving dysfunction of the central nervous systems including stroke or traumatic brain injury, spinal cord injury, cerebral palsy and other condition, which result in debilitation of the nervous system. The treatment may incorporate continuous stimulation for some period of time such as four to eight, or around six hours per day. Since the therapy is passive and relatively free from pain, the patient may undergo treatment while otherwise conducting life as usual.

EXAMPLES

In order to assess the clinical feasibility of percutaneous, intramuscular NMES for treating shoulder dysfunction in hemiplegia, three studies were carried out in our laboratory. The first study compared the level of discomfort associated with intramuscular and transcutaneous NMES during reduction of shoulder subluxation. The second study was a pilot study investigating the effects of percutaneous, intramuscular NMES on shoulder subluxation, range of motion, pain, motor recovery and disability in persons with chronic hemiplegia and shoulder subluxation. The third study was a preliminary study to determine whether the muscles previously selected in the transcutaneous NMES studies are, in fact, the muscles which provide maximal reduction of shoulder subluxation.

Example 1

To compare stimulation-induced pain between transcutaneous and percutaneous, intramuscular NMES, 10 subjects were enrolled with hemiplegia and at least one fingerbreadth of shoulder subluxation. A cross over study design was used. Each subject received 3 pairs of randomly ordered transcutaneous or intramuscular stimulation. Both types of stimulation were modulated to provide full joint reduction by palpation with the least discomfort. Subjects were blinded to the type of stimulation given. The evaluator was blinded to the type of stimulation given when assessing joint reduction by palpation and when administering the pain measures. Pain was measured using a 10 cm visual analogue scale and the McGill Pain Questionnaire using the pain rating index (PRI) method for quantification of data. The pain descriptors of the McGill Pain Questionnaire were read aloud to subjects during each administration. Pain measures were obtained immediately after each of the six stimulations. After the last pair of stimulations, the subjects were asked which of the last pair they would prefer for six weeks of treatment at six hours per day.

Figure 5:
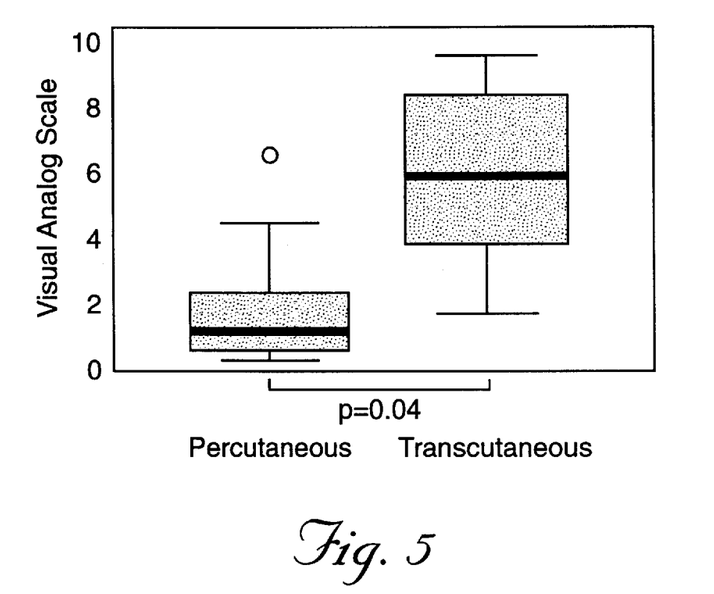
FIG. 5 is a graphic illustration of the results of the study of Example 1.
Figure 6:
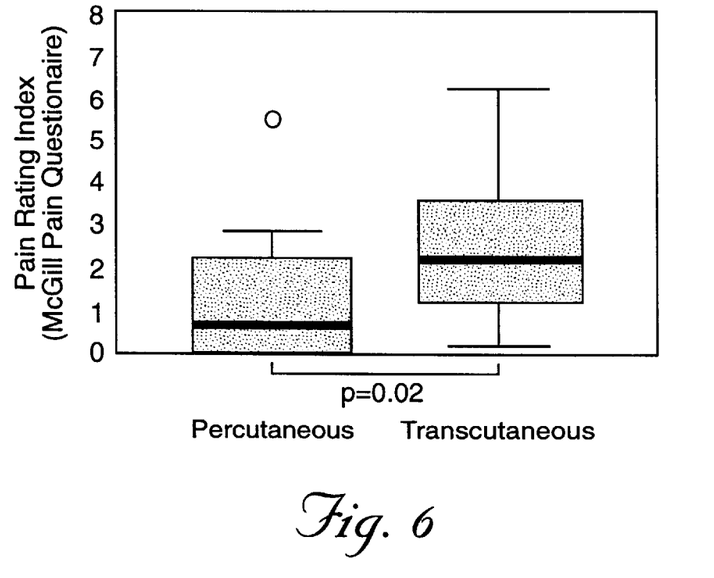
FIG. 6 is a second graphic illustration of the results of the study of Example 1.
Figure 7:
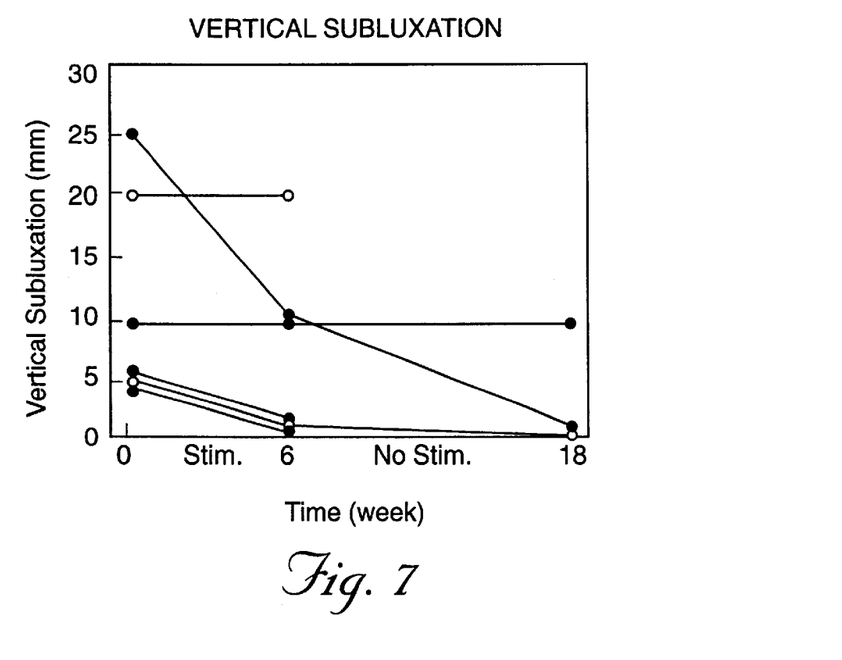
FIG. 7 is a graphic illustration of the results of the study of Example 2.
Figure 8:
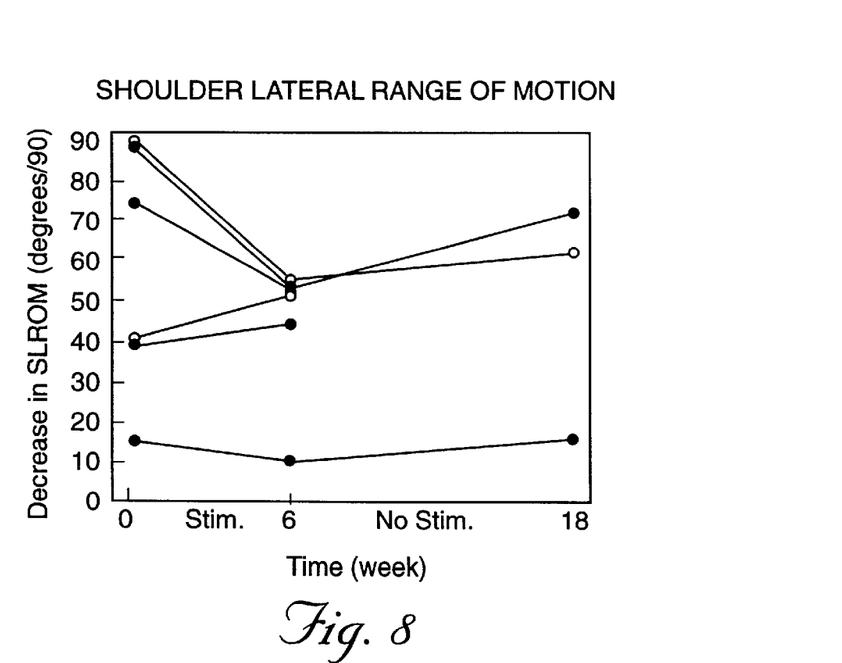
FIG. 8 is a second graphic illustration of the results of the study of Example 2.
Figure 9:
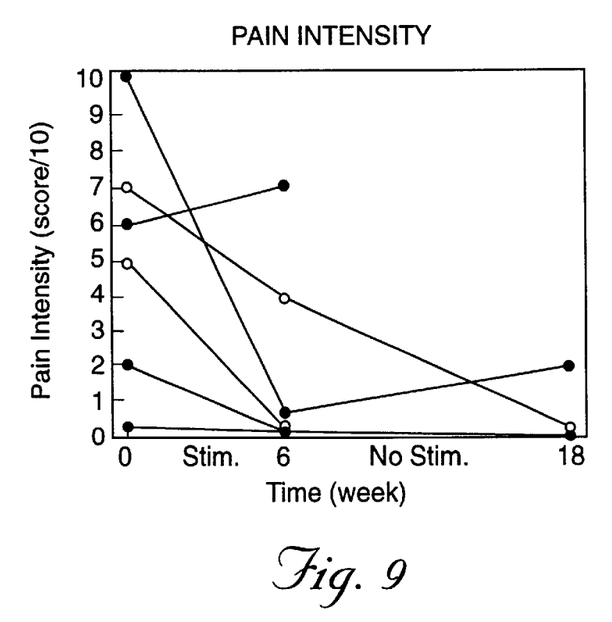
FIG. 9 is a third graphic illustration of the results of the study of Example 2.
Figure 10:
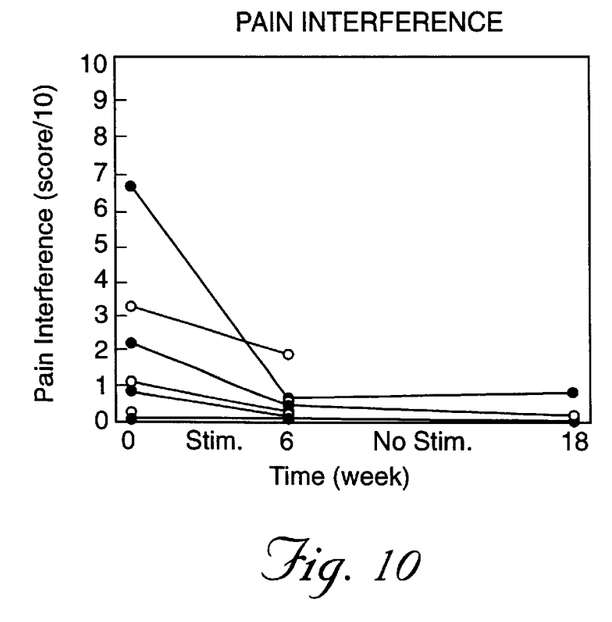
FIG. 10 is a fourth graphic illustration of the results of the study of Example 2.
Figure 11:
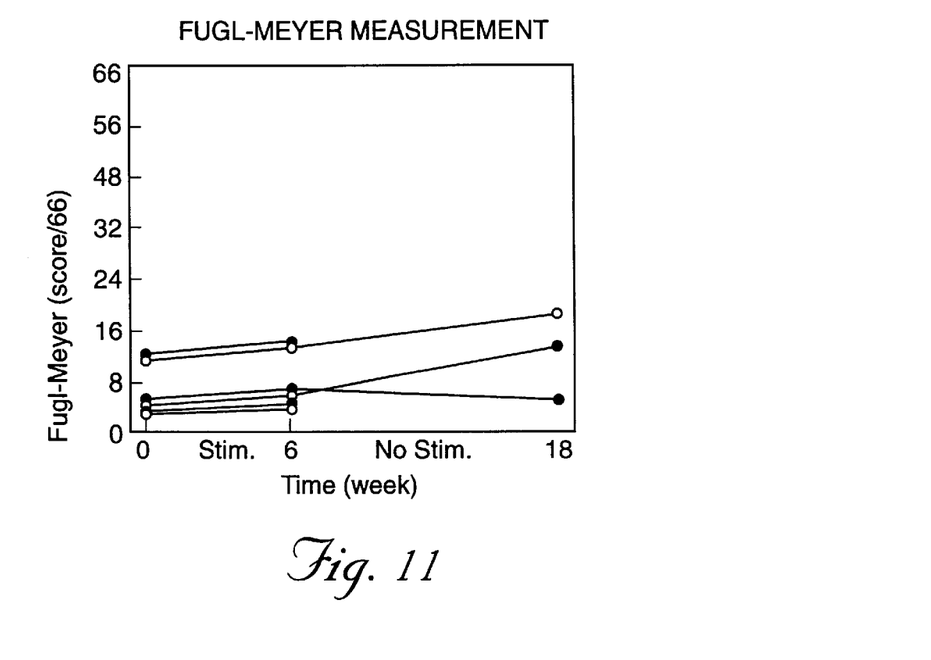
FIG. 11 is a fifth graphic illustration of the results of the study of Example 2.
Figure 12:
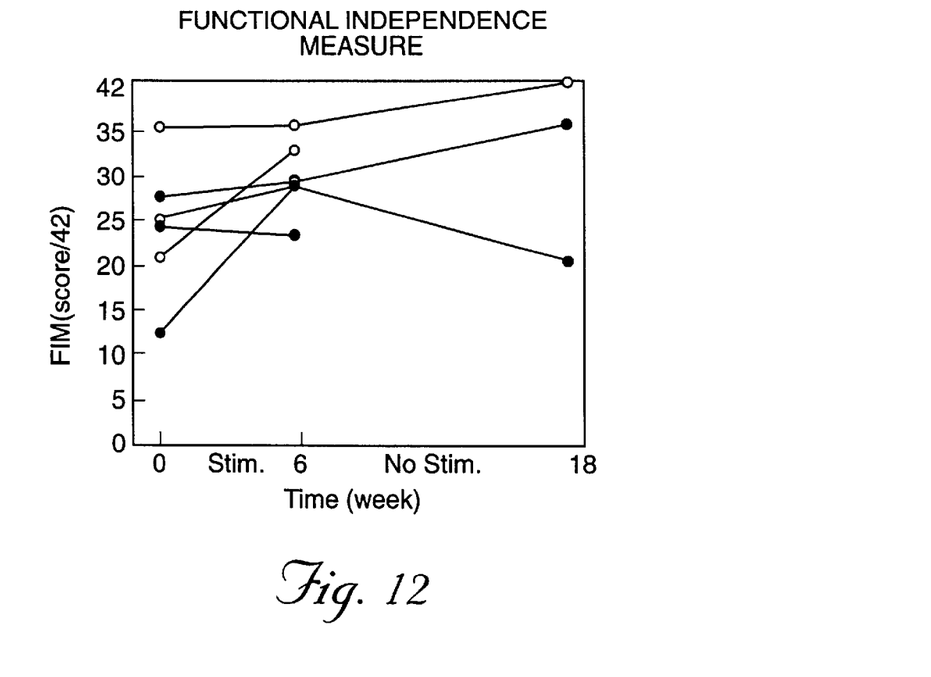
FIG. 12 is a sixth graphic illustration of the results of the study of Example 2.

The results are summarized in FIGS. 5 and 6. Significantly less pain was experienced during percutaneous, intramuscular NMES than during transcutaneous NMES. Nine of 10 subjects preferred intramuscular over transcutaneous stimulation. This study assessed discomfort with two types of NMES taking into account two critical factors in studying pain with NMES. First, the stimulation induced pain was measured during the clinical application. Stimulus parameters differ depending on the application and may have a significant affect on the discomfort experienced during stimulation. For example, the current and frequency required for weight bearing activities such as ambulation are much greater than those needed for reducing shoulder subluxation. Secondly, the stimulation was administered in the target population. The perception of pain may potentially be altered based on differences in the underlying neural pathophysiology. Though these results demonstrate less pain with percutaneous, intramuscular stimulation, they only infer that treatment with percutaneous, intramuscular NMES is better tolerated than treatment with transcutaneous NMES.

Example 2

The effects of percutaneous intramuscular NMES was investigated on shoulder subluxation, range of motion, pain, motor recovery and disability in persons with chronic hemiplegia and shoulder subluxation. In a pre-test, post-test trial, 8 neurologically stable subjects received 6 weeks of intramuscular NMES for 6 hours per day. A pager sized stimulator which could be worn on the belt or placed in a pocket was designed for this application to allow the subjects to receive treatment without interfering with mobility and daily activities. Inferior and lateral shoulder subluxation was quantified with an unvalidated radiographic technique. Radiographs of both shoulders were obtained. The difference in glenohumeral translation between the subluxated and unaffected shoulder was measured to take into account normal variance among individuals. Pain free passive shoulder external rotation was measured using a hand held goniometer in the supine, relaxed subject. Shoulder pain was quantified using the Brief Pain Inventory (BPI), which evaluates pain intensity and interference with daily activities. The BPI has been validated for quantifying cancer pain but has not been validated in hemiplegia or regional shoulder pain. Motor impairment was measured using the upper limb portion of the Fugl-Meyer Scale (FMS). The self-care portion of the Functional Independence Measure™ (FIM) was used to evaluate disability. Testing was performed prior to administering 6 weeks of intramuscular NMES (T1), after completing the 6-week treatment (T2) and at a 3 month follow-up (T3.) The Wilcoxon Sign Rank Test was used to determine the statistical significance of differences between T1 and T2 and between T2 and T3 for all outcomes. Questionnaires to assess tolerance and ease of implementation were developed after the study had begun and were administered to half of the users and caregivers.

The results are summarized in FIGS. 7–12. Vertical subluxation, range of motion, shoulder pain and self-care skills all improved significantly from pre-treatment to post-treatment. The reduction in joint subluxation was maintained at 3 months. Shoulder pain increased and range of motion decreased from post-treatment to the 3-month follow-up but the changes were not statistically significant. Self-care skills improved non-significantly from post-treatment to 3-month follow-up. The self-care portion of the FIM was not a good choice for measurement of disability in this population because the self-care tasks can be performed independently with a single intact upper limb. In this study, improvements in FIM scores may not be due to motor recovery and did not parallel changes in FMS. However, the improved FIM scores may reflect changes due to other effects of the intervention such as decreased pain or confounders such as increased motivation. A trend in improvement of motor function was seen after treatment but was only statistically significant at the 3-month follow-up. The median time since onset of hemiplegia in the subjects studied was 11 months with a range of six to 28 months. Though unlikely, some motor improvement may have been due to natural recovery. Improved FMS were documented in some subjects with flaccid hemiplegia for 2 years or more. Responses to the questionnaires indicated that the treatment was well tolerated, required less than 5 minutes per day to don and doff, did not interfere with daily activities and was preferred over the use of a sling.

Example 3

The third study determined whether the standard muscles targeted for stimulation provide the best reduction of shoulder subluxation. The supraspinatus and posterior deltoid muscles were stimulated in the previously discussed transcutaneous NMES studies. These muscles were selected based on a study by Basmajian et al. In his study, EMG activity in the shoulder muscles of normal adults were observed during rest and inferiorly directed traction on the upper limb. The supraspinatus was found to be uniformly active and the posterior deltoid less active under these conditions. In our pilot experience with intramuscular NMES for treating shoulder subluxation, the supraspinatus did not consistently reduce subluxation during stimulation. A preliminary survey of various shoulder muscles was undertaken to determine whether other muscles may provide better joint reduction during stimulation. Up to 13 shoulder muscles were stimulated in 12 subjects with hemiplegia and at least one fingerbreadth of shoulder subluxation. Muscle selection for testing was based on accessibility for implantation of percutaneous electrodes and the force vectors between the scapula and humueral head generated during muscle contraction. The stimulus was titrated to avoid pain and unwanted joint movement (e.g. active elbow flexion during biceps stimulation). Joint reduction was assessed by palpation in all subjects and radiographically in two subjects using a three-dimensional technique that standardizes trunk and limb position, uses the glenoid fossa as a reference frame and measures the difference in joint translation between the affected and unaffected shoulders. Stimulation of the supraspinatus muscle provided incomplete reduction of subluxation. Several other muscles provided more complete and more consistent joint reduction including all heads of the deltoid, the coracobrachialis, the biceps and the triceps long head. While radiographic inferior subluxation correlated well with palpation, the three-dimensional technique correlated poorly with subluxation measured by palpation. This discrepancy was felt to be due to inadequate assessment of anterior subluxation by palpation.

While in accordance with the Patent Statutes the best mode and preferred embodiment have been set forth, the scope of the invention is not limited thereto but rather by the scope of the attached claims.

What is claimed is:

1. A method of stimulating select shoulder muscle tissue of a patient for the treatment of shoulder dysfunction comprising:

evaluating the shoulder for subluxation;

implanting an intramuscular electrode into select muscle tissue;

programming a stimulation pulse generator in communication with said electrode with at least one stimulation pulse train pattern including at least one stimulation cycle defining a stimulation pulse train envelope; and addressing the electrode with the pulse train generator to stimulate the muscle tissue and thereby treat the subluxation.

2. A method of stimulating shoulder select muscle tissue as set forth in claim 1, wherein each of said pulse train envelopes is defined by at least a ramp-up phase of a first select duration in which the pulses of a stimulus pulse train progressively increase in charge, a hold phase of a second select duration in which the pulses of the stimulus pulse train are substantially constant charge, and a ramp-down phase of a third select duration in which the pulses of the stimulus pulse train progressively decrease in charge.

3. A method of stimulating select shoulder muscle tissue as set forth in claim 1, wherein said implanting step comprises implanting a plurality of intramuscular electrodes into select muscle tissue of the patient;

electrically connecting said plurality of intramuscular electrodes implanted into patient muscle tissue to a plurality of output channels, respectively; and, generating stimulation pulse train signals with said generator for each of said plurality of stimulation output channels so that said select muscle tissue of said patient is stimulated in accordance with said at least one stimulation cycle and wherein said select muscle tissue is at least two different muscle tissues.

4. A method of stimulating select shoulder muscle tissue as set forth in claim 3, wherein at least two stimulation pulse train signals are generated to form at least two stimulation cycles which are not equal at every point in time.

5. The method of stimulating select shoulder muscle tissue of a patient as set forth in claim 3, wherein said step of implanting a plurality of intramuscular electrodes into patient muscle tissue includes implanting up to eight intramuscular electrodes.

6. The method of stimulating select shoulder muscle tissue of a patient as set forth in claim 1, wherein said evaluation of the shoulder comprising a radiographic evaluation of the shoulder area for subluxation of the shoulder of the patient to select muscle for treatment.

7. The method of stimulating select shoulder muscle tissue of a patient as set forth in claim 6, wherein the patient is hemiplegic and the method further includes a comparison of a first shoulder involving the select muscle tissue with the other shoulder of the patient.

8. The method of stimulating select shoulder muscle tissue of a patient as set forth in claim 1, wherein said pulse train signals are generated so as to provide for stimulation for at least one hour every day for a period of treatment.

9. The method of stimulating select shoulder muscle tissue of a patient as set forth in claim 6, wherein said evaluation includes assessment in at least two planes selected from the group consisting of anterior/posterior; medical/lateral, and superior inferior.

10. The method of stimulating select muscle tissue of a patient as set forth in claim 8, wherein said period of treatment is at least one week.

11. The method of stimulating select muscle tissue as set forth in claim 1, wherein said muscle tissue is selected from the supraspinatus, the posterior deltoid, the middle deltoid, the anterior deltoid, the coracobrachialis, the biceps, and triceps and the upper trapezious.

12. A method of stimulating select muscle tissue as set forth in claim 1, wherein said stimulation pulse train envelope is a balance charge wave form.

13. A method of stimulating select muscle tissue as set forth in claim 1, wherein said evaluation of subluxation is evaluated as result of a central nervous disorder.

14. A method of stimulating select muscle tissue as set forth in claim 13, wherein said evaluation as a result of a central nervous disorder is evaluated as one or more of stroke, traumatic brain injury, spinal cord injury, and cerebral palsy.

* * * * *

UNITED STATES PATENT AND TRADEMARK OFFICE
CERTIFICATE OF CORRECTION

| | |
|---|---|
| PATENT NO. | : 6,845,271 B2 |
| APPLICATION NO. | : 10/138791 |
| DATED | : January 18, 2005 |
| INVENTOR(S) | : Zi-Ping Fang and Maria Walker |

It is certified that error appears in the above-identified patent and that said Letters Patent is hereby corrected as shown below:

On the title of the Issued Patent under item [56], "Other Publications" insert the following article: – P. Crago, "Control of Movements by Functional Neuromuscular Stimulation", Eng. In Med. and Biol. Magazine, Sept. 1983, pp. 32-36. --

Signed and Sealed this

Fifteenth Day of August, 2006

JON W. DUDAS
*Director of the United States Patent and Trademark Office*